US012582472B2

(12) United States Patent
Lim et al.

(10) Patent No.: US 12,582,472 B2
(45) Date of Patent: Mar. 24, 2026

(54) SYSTEMS FOR DETERMINING SIZE OF KIDNEY STONE

(71) Applicant: Boston Scientific Scimed, Inc., Maple Grove, MN (US)

(72) Inventors: Kian Lim, Shrewsbury, MA (US); Longquan Chen, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 499 days.

(21) Appl. No.: 17/931,824

(22) Filed: Sep. 13, 2022

(65) Prior Publication Data

US 2023/0092920 A1      Mar. 23, 2023

Related U.S. Application Data

(60) Provisional application No. 63/261,340, filed on Sep. 17, 2021.

(51) Int. Cl.
 *A61B 18/22*          (2006.01)
 *A61B 1/307*          (2006.01)
      (Continued)

(52) U.S. Cl.
 CPC ............... *A61B 18/22* (2013.01); *A61B 1/307* (2013.01); *A61B 2018/00511* (2013.01); *A61B 2018/00982* (2013.01)

(58) Field of Classification Search
 CPC .............. A61B 1/00071; A61B 1/0008; A61B 1/00087; A61B 1/00096; A61B 1/00097;
      (Continued)

(56) References Cited

U.S. PATENT DOCUMENTS 3,817,635 A * 6/1974 Kawahara .......... A61B 1/00165
                                                  356/11
3,819,267 A * 6/1974 Kawahara .......... G02B 23/2438
                                                  356/3
(Continued)

FOREIGN PATENT DOCUMENTS

EP          1 496 709 B1      9/2010
GB          1233604 A  *    5/1971
      (Continued)

OTHER PUBLICATIONS

Peng, Hui. "Experimental Study of Mystery of Double Slit— Comprehensive Double Slit Experiments." International Journal of Physics 9.2 (2021): 114-127 (Year: 2021).*
      (Continued)

*Primary Examiner* — Anne M Kozak
*Assistant Examiner* — Jason P Gross
(74) *Attorney, Agent, or Firm* — Bookoff McAndrews, PLLC

(57)          ABSTRACT

A system is disclosed that includes an optical fiber including a first optical module and a gate. The gate can be capable of moving between closed and opened states to form a slit. At least one storage medium can be included having encoded thereon executable instructions that, when executed by the at least one processor, cause the system to carry out a method including directing light from the first optical module through the slit onto the stone to form a pair of lines with a spacing between the pair of lines; and determining a size of the stone, based on a distance from a distal tip of the optical fiber and the spacing between the pair of lines.

18 Claims, 10 Drawing Sheets

(51) Int. Cl.
    *A61B 5/107*         (2006.01)
    *A61B 18/00*         (2006.01)

(58) Field of Classification Search
    CPC ............ A61B 1/00101; A61B 1/00137; A61B
               1/00147; A61B 1/00163; A61B 1/00165;
               A61B 1/00167; A61B 1/0017; A61B
               1/04; A61B 1/05; A61B 1/07; A61B
               1/307; A61B 5/103; A61B 5/107; A61B
               5/1072; A61B 5/1075; A61B 5/1076;
               A61B 2018/2035; A61B 2018/2255;
               A61B 18/245; A61B 18/26; A61B
               2018/20357; A61B 2018/20359; A61B
               2018/205545; A61B 2018/205547; A61B
               90/06; A61B 90/361; A61B 2090/306;
               A61B 2090/3614; A61B 2090/364; A61B
               2090/365; A61B 2090/366; A61B
               2090/367; A61B 2090/373; A61B
               2090/3945; A61B 5/6886; G01S 17/06;
               G01S 17/08; G01S 17/42; G01S 17/46;
               G01S 17/48; G02B 23/24; G06T 3/40;
               H04N 7/0122
    See application file for complete search history.

(56)                References Cited

U.S. PATENT DOCUMENTS

| | | | | |
|---|---|---|---|---|
| 4,834,071 | A * | 5/1989 | Hosoi | A61B 1/0655 |
| | | | | 348/E5.038 |
| 4,986,262 | A * | 1/1991 | Saito | A61B 1/0661 |
| | | | | 600/475 |
| 5,042,915 | A * | 8/1991 | Akutsu | A61B 1/07 |
| | | | | 359/290 |
| 5,237,403 | A * | 8/1993 | Sugimoto | G02B 26/04 |
| | | | | 348/69 |
| 5,630,809 | A * | 5/1997 | Connor | A61F 9/007 |
| | | | | 606/4 |
| 5,669,871 | A * | 9/1997 | Sakiyama | G01B 11/22 |
| | | | | 348/136 |
| 5,910,845 | A * | 6/1999 | Brown | G01B 11/25 |
| | | | | 356/608 |
| 2007/0161854 | A1 * | 7/2007 | Alamaro | A61B 1/0676 |
| | | | | 600/109 |

| | | | | |
|---|---|---|---|---|
| 2008/0243108 | A1 * | 10/2008 | Murakami | A61F 9/008 |
| | | | | 606/4 |
| 2009/0073404 | A1 * | 3/2009 | Muramatsu | G03F 7/70466 |
| | | | | 430/311 |
| 2009/0244260 | A1 * | 10/2009 | Takahashi | A61B 5/0064 |
| | | | | 348/E13.001 |
| 2009/0270682 | A1 * | 10/2009 | Visser | A61B 90/06 |
| | | | | 600/160 |
| 2011/0190760 | A1 * | 8/2011 | Niver | A61B 90/37 |
| | | | | 606/33 |
| 2015/0305603 | A1 * | 10/2015 | Gal | A61B 1/0669 |
| | | | | 600/109 |
| 2016/0287141 | A1 * | 10/2016 | Sidlesky | G02B 23/2415 |
| 2018/0098053 | A1 * | 4/2018 | Imade | G03B 11/00 |
| 2018/0103246 | A1 * | 4/2018 | Yamamoto | A61B 1/04 |
| 2018/0199795 | A1 * | 7/2018 | Maruyama | A61B 1/0057 |
| 2019/0204069 | A1 * | 7/2019 | Tatsuta | G06T 7/0012 |
| 2019/0374155 | A1 * | 12/2019 | Wang | A61B 1/2736 |
| 2021/0038306 | A1 * | 2/2021 | McLoughlin | A61B 5/0084 |
| 2021/0196398 | A1 * | 7/2021 | Ye | A61B 5/0084 |
| 2021/0196424 | A1 * | 7/2021 | Shelton, IV | G16H 20/40 |

FOREIGN PATENT DOCUMENTS

| | | |
|---|---|---|
| JP | S59-151119 A | 8/1984 |
| JP | 2005-279028 A | 10/2005 |
| WO | WO 2019/046237 A1 | 3/2019 |

OTHER PUBLICATIONS

Ji X, Ferreira T, Friedman B, Liu R, Liechty H, Bas E, Chandrashekar J, Kleinfeld D. Brain microvasculature has a common topology with local differences in geometry that match metabolic load. Neuron. Apr. 7, 2021;109(7):1168-87. (Year: 2021).*

Dunn, Stanley M., Richard L. Keizer, and Jongdaw Yu. "Measuring the area and volume of the human body with structured light." IEEE transactions on systems, man, and cybernetics 19.6 (1989): 1350-1364 (Year: 1989).*

Zhixin, Hu, et al. "Adaptive centre extraction method for structured light stripes." Ukrainian journal of physical optics 18,â 1 (2017): 9-19 (Year: 2017).*

International Search Report and Written Opinion in International Application No. PCT/US2022/076373, dated Dec. 23, 2022 (11 pages).

* cited by examiner

DIRECTING LIGHT FROM A FIRST OPTICAL MODULE
OF AN OPTICAL FIBER THROUGH A SLIT ONTO THE
STONE TO FORM A PAIR OF LINES
610

DETERMINING A SIZE OF THE STONE, BASED ON A
DISTANCE FROM A DISTAL TIP OF THE OPTICAL FIBER
AND A SPACING BETWEEN THE PAIR OF LINES
620

700

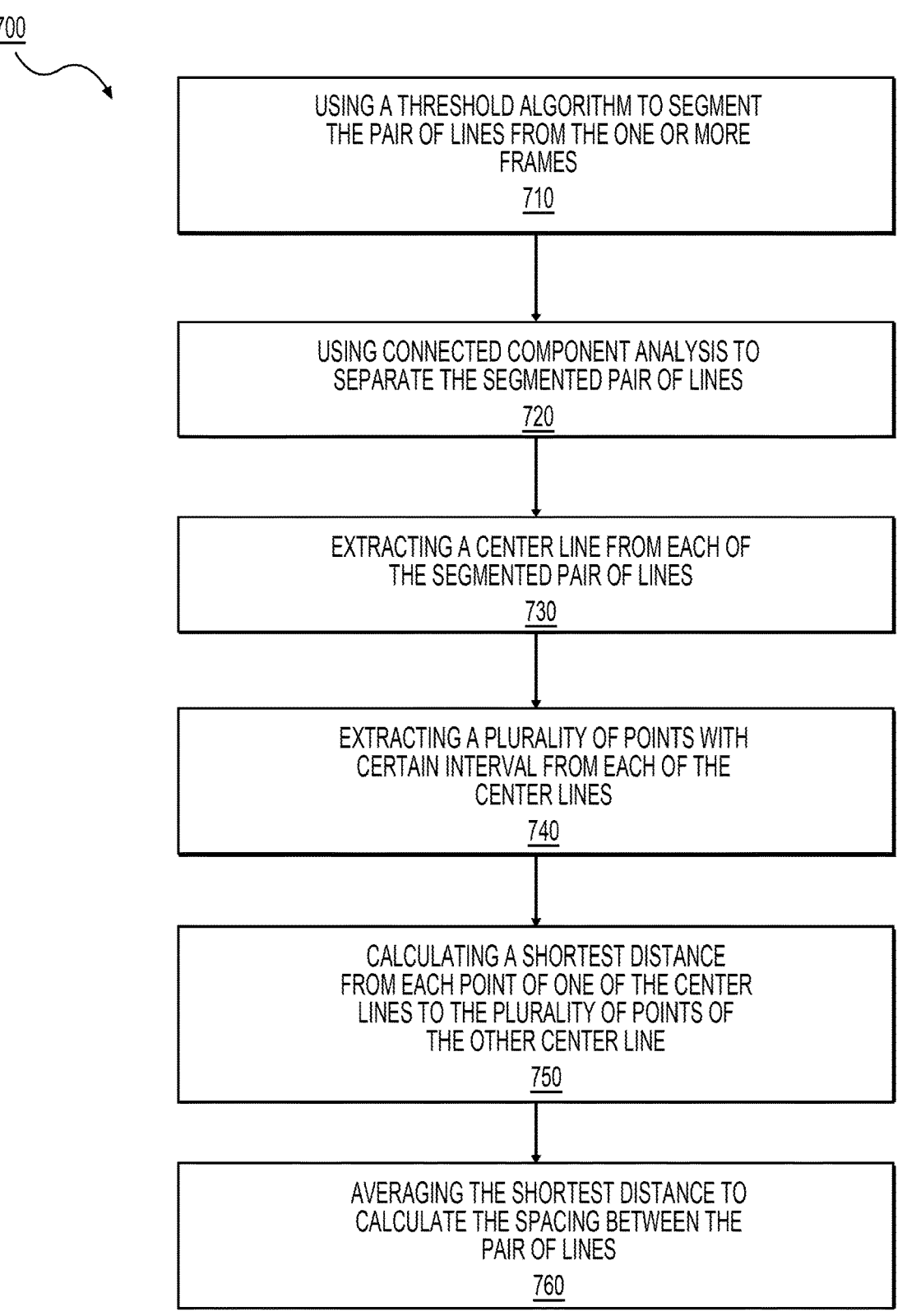

USING A THRESHOLD ALGORITHM TO SEGMENT
THE PAIR OF LINES FROM THE ONE OR MORE
FRAMES
710

USING CONNECTED COMPONENT ANALYSIS TO
SEPARATE THE SEGMENTED PAIR OF LINES
720

EXTRACTING A CENTER LINE FROM EACH OF
THE SEGMENTED PAIR OF LINES
730

EXTRACTING A PLURALITY OF POINTS WITH
CERTAIN INTERVAL FROM EACH OF THE
CENTER LINES
740

CALCULATING A SHORTEST DISTANCE
FROM EACH POINT OF ONE OF THE CENTER
LINES TO THE PLURALITY OF POINTS OF
THE OTHER CENTER LINE
750

AVERAGING THE SHORTEST DISTANCE TO
CALCULATE THE SPACING BETWEEN THE
PAIR OF LINES
760

*FIG. 10*

SYSTEMS FOR DETERMINING SIZE OF KIDNEY STONE

CROSS-REFERENCE TO RELATED APPLICATIONS

This patent application claims the benefit of priority under 35 U.S.C. § 119 to U.S. Provisional Patent Application No. 63/261,340, filed Sep. 17, 2021, which is herein incorporated by reference in its entirety.

TECHNICAL FIELD

This disclosure relates generally to systems and methods for minimally invasive medical procedures within a patient's body cavity. More particularly, embodiments of the present disclosure relate to devices and methods to identify information related to a target (e.g., a stone, foreign object, and/or tissue) within a patient's body.

BACKGROUND

Urolithiasis is a condition in which a kidney stone forms within a person's urinary tract. A kidney stone is a small hard stone that can cause pain, bleeding, obstruction, or infection. A kidney stone forms from deposits of calcium, phosphates, and urates.

Kidney stones can vary in size. Ureteroscopy often requires extraction of stone fragments by grasping them in a basket and pulling them out of the body along the ureteral tract. For example, smaller stones can have a greater chance to pass through the urinary tract and out of the body. Bigger stones in contrast may need to be retrieved by memory alloyed wire baskets device through a ureteroscope or even broken up into smaller pieces with lithotripsy.

Urologists occasionally attempt to remove such stone fragments only to find that the fragment is too large to remove through the ureter, since endoscopic stone fragment size estimates are subjective and can be in error. Urologists often struggle to determine which method is plausible, safe, and effective for a particular stone. Current approaches fail to provide adequate information related to the kidney stone to guide urologists in accurately devising treatments for a particular patient.

Therefore, there exists a continuing need for devices that can accurately communicate to an operator information related to a kidney stone. The solution of this disclosure resolves these and other issues of the art.

SUMMARY

In accordance with certain aspects of the present disclosure, a system is disclosed for analyzing in vivo a kidney stone. It is noted that while the system of this disclosure is described principally analyzing kidney stone(s), it is contemplated that the system can also be used to analyze in vivo other objects in a patient, including but not limited to a gall stone, a stone present in a salivary tract, a stone present in a biliary tract, a pancreatic stone, and a vascular stone. The system can include a probe including an optical fiber including a first optical module and a slit gate. The slate gate can be capable of moving between closed and opened states to form a slit. At least one storage medium can be included having encoded thereon executable instructions that, when executed by the at least one processor, cause the system to carry out a method including directing light from the first optical module through the slit onto the stone to form a pair of lines with a spacing formed between the pair of lines; and determining a size of the stone, based on a distance from a distal tip of the optical fiber and the spacing between the pair of lines.

In accordance with certain aspects of the present disclosure, the slit includes a vertical line.

In accordance with certain aspects of the present disclosure, the slit includes a crisscross line.

In accordance with certain aspects of the present disclosure, the slit includes at least three lines with a common intersection.

In accordance with certain aspects of the present disclosure, the optical fiber includes a second optical module configured to be used for lithotripsy.

In accordance with certain aspects of the present disclosure, the probe has one or more fibers configured as Power Over Fiber Systems (PoF).

In accordance with certain aspects of the present disclosure, the optical fiber is a multiple core fiber with at least two fiber cores lighted up by a high-power LED module inside a handle of a ureteroscope.

In accordance with certain aspects of the present disclosure, the system includes an amplifier electrically coupled to the at least two fiber cores and the high-power LED module.

In accordance with certain aspects of the present disclosure, the optical fiber is a multiple core fiber including at least two fiber cores lighted up by a laser inside a handle of a Ureteroscope.

In accordance with certain aspects of the present disclosure, the optical fiber includes a camera.

In accordance with certain aspects of the present disclosure, the at least one processor is configured to carry out the method that includes focusing, by the first optical module, the pair of lines onto the stone.

In accordance with certain aspects of the present disclosure, the at least one processor is configured to carry out the method that includes receiving, from a camera of the optical fiber, one or more images of the stone; and calculating the spacing between the lines by applying one or more image processing algorithms to extract information from one or more frames of the one or more images.

In accordance with certain aspects of the present disclosure, the step of applying one or more image processing algorithms includes analyzing an object near distance of the optical fiber and a near laser gap.

In accordance with certain aspects of the present disclosure, the step of applying one or more image processing algorithms includes analyzing an object far distance and a far laser gap of the optical fiber.

In accordance with certain aspects of the present disclosure, the step of applying one or more image processing algorithms includes analyzing a known laser distance and a known laser spacing of the optical fiber.

In accordance with certain aspects of the present disclosure, the step of applying one or more image processing algorithms includes analyzing a focal length of the camera in communication with the first optical module by comparing a pixel with a distance from the stone and a width of the stone.

In accordance with certain aspects of the present disclosure, the step of applying one or more image processing algorithms includes using a threshold algorithm to segment the pair of lines from the one or more frames; using connected component analysis to separate the segmented pair of lines; extracting a center line from each of the segmented pair of lines; extracting a plurality of points with certain interval from each of the center lines; calculating a shortest distance from each point of one of the center lines to the plurality of points of the other center line; and averaging the shortest distance to calculate the spacing between the pair of lines.

In accordance with certain aspects of the present disclosure, the pair of lines are curved due to one or more uneven surfaces of the stone.

In accordance with certain aspects of the present disclosure, the spacing between the pair of lines varies with respect to the distance of the optical fiber from the stone.

In accordance with certain aspects of the present disclosure, the spacing is smaller as the optical fiber is closer to the stone.

In accordance with certain aspects of the present disclosure, the spacing is larger as the optical fiber is further from the stone.

In accordance with certain aspects of the present disclosure, the step of determining the size of the stone includes determining a spacing between fibers of the optical fiber.

In accordance with certain aspects of the present disclosure, the step of determining the size of the stone includes determining a thickness and a length of the slit.

In accordance with certain aspects of the present disclosure, a method is disclosed for analyzing in vivo a kidney stone. The method can include directing light from a first optical module of an optical fiber through a slit onto the stone to form a pair of lines; and determining a size of the stone, based on a distance from a distal tip of the optical fiber and a spacing between the pair of lines.

In accordance with certain aspects of the present disclosure, the method can include focusing, by the first optical module, the pair of lines onto the stone with a spacing between the pair of lines.

In accordance with certain aspects of the present disclosure, the method can include using a second optical module of the optical fiber to perform lithotripsy.

In accordance with certain aspects of the present disclosure, the second optical module is used to perform lithotripsy while the first optical module directs light through the slit onto the stone to form the pair of lines.

In accordance with certain aspects of the present disclosure, the method can include wrapping the pair of lines around the stone to generate a visual topography.

In accordance with certain aspects of the present disclosure, the method can include calibrating a camera coupled with the optical fiber with respect to the pair of lines to determine a depth between the camera and the pair of lines; and determining, by the calibrated camera, a size of the stone, based on the depth.

In accordance with certain aspects of the present disclosure, the method can include receiving, from a camera of the optical fiber, a one or more images of the stone; and calculating the spacing between the lines by applying one or more image processing algorithms to extract information from one or more frames of the one or more images.

In accordance with certain aspects of the present disclosure, the step of applying one or more image processing algorithms includes analyzing an object near distance of the optical fiber and a near laser gap.

In accordance with certain aspects of the present disclosure, the step of applying one or more image processing algorithms includes analyzing an object far distance and a far laser gap of the optical fiber.

In accordance with certain aspects of the present disclosure, the step of applying one or more image processing algorithms includes analyzing a known laser distance and a known laser spacing of the optical fiber.

In accordance with certain aspects of the present disclosure, the step of applying one or more image processing algorithms includes analyzing a focal length of the camera in communication with the first optical module by comparing a pixel with a distance from the stone and a width of the stone.

In accordance with certain aspects of the present disclosure, the method can include presenting a notification indicating the size of the stone to a user, the notification including an audio and/or a visual indication.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The accompanying drawings, which are incorporated in and constitute a part of this specification, illustrate various exemplary aspects of the disclosure, and together with the description serve to explain the principles of the present disclosure.

FIG. 5B illustrates a front plan view of a fiber of FIG. 5A with a slit pattern.

FIG. 5C illustrates a front plan view of a fiber of FIG. 5A with a slit pattern.

FIG. 5D illustrates a front plan view of a fiber of FIG. 5A with a slit pattern.

FIG. 10 depicts a flow diagram of a method of using a system to analyze a target according to certain aspects of this disclosure.

DETAILED DESCRIPTION

Figure 1:
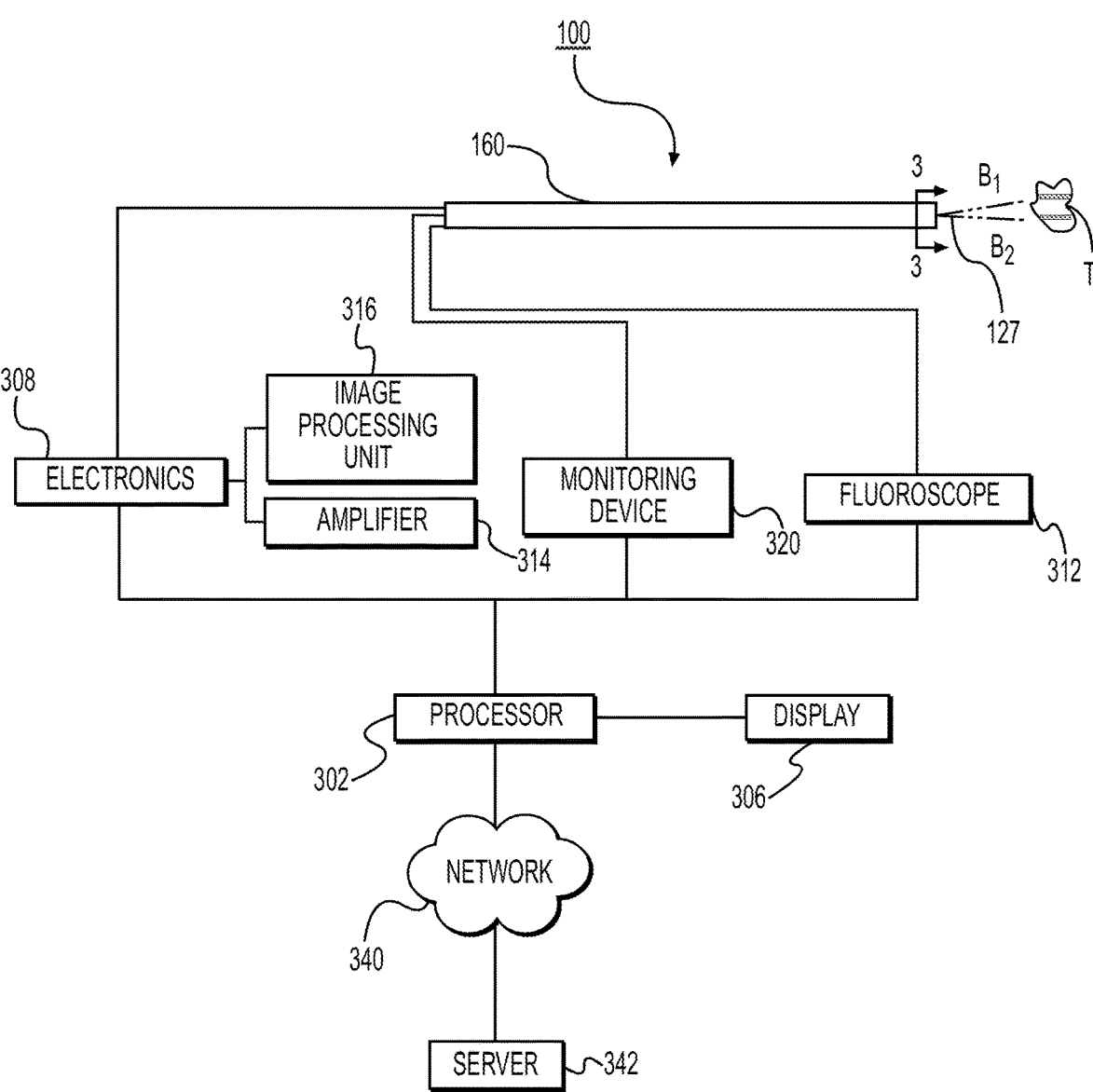
FIG. 1 shows a schematic view of an exemplary system in accordance with certain aspects of the present disclosure.

Particular aspects of the present disclosure are described in greater detail below. The terms and definitions provided herein control, if in conflict with terms and/or definitions incorporated by reference.

Particular aspects of the present disclosure may repeat reference numerals and/or letters in the various examples. This repetition is for the purpose of simplicity and clarity and does not in itself dictate a relationship between the various embodiments and/or configurations discussed. Different embodiments may have different advantages, and no particular advantage is necessarily required of any embodiment.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal."

As used herein, the singular forms "a," "an," and "the" include plural reference unless the context dictates otherwise.

As used herein, "approximately" and "about" refer to being nearly the same as a referenced number or value. As used herein, the terms "approximately" and "about" should be understood to encompass ±10% of a specified amount or value (e.g., "about 90%" can refer to the range of values from 81% to 99%.

As used herein, "operator" can include a doctor, surgeon, or any other individual or delivery instrumentation associated with delivery or use of a mixing system as such systems are described throughout this disclosure.

As used herein, when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

Examples of the present disclosure relate to devices and methods for controlling the application of energy to objects disposed within a body lumen of a patient, such as, e.g., a lumen of a kidney, a bladder, or a ureter.

It is understood that the present disclosure may be embodied as methods, systems, and/or computer program products. Accordingly, the present disclosure may take the form of an entirely hardware embodiment, an entirely software embodiment or an embodiment combining software and hardware aspects. Furthermore, the present disclosure may take the form of a computer program product on a computer-usable storage medium having computer-usable program code embodied in the medium. Any suitable computer readable medium may be utilized including hard disks, CD-ROMs, optical storage devices, or magnetic storage devices.

The computer-usable or computer-readable medium referred to herein as "memory" may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

The disclosure is also described using flowchart illustrations and block diagrams. It will be understood that each block (of the flowcharts and block diagrams), and combinations of blocks, can be implemented by computer program instructions. These program instructions may be provided to a processor circuit, such as a microprocessor, microcontroller or other processor, such that the instructions which execute on the processor(s) create means for implementing the functions specified in the block or blocks. The computer program instructions may be executed by the processor(s) to cause a series of operational steps to be performed by the processor(s) to produce a computer implemented process such that the instructions which execute on the processor(s) provide steps for implementing the functions specified in the block or blocks.

It is understood that the blocks support combinations of means for performing the specified functions, combinations of steps for performing the specified functions and program instruction means for performing the specified functions. It will also be understood that each block, and combinations of blocks, can be implemented by special purpose hardware-based systems which perform the specified functions or steps, or combinations of special purpose hardware and computer instructions.

FIG. 1 illustrates system 100 for delivering energy, in accordance with a first example of the present disclosure. System 100 can include an optical fiber 160 (e.g., laser fiber) and may be configured to deliver energy 127 at a distal end towards a target T (e.g., a stone, foreign object, and/or tissue). Fiber 160 can include one or more channels to transmit light beams $B_1$, $B_2$ or receive light from or related to one or more target images of target T. In some aspects, fiber 160 can withstand tortuous conditions of a patient (e.g., as part of a flexible catheter) and deliver energy 127 from its distal tip when adjacent target T. One or more LEDs or laser diodes can be placed in a handle of system 100 in communication with fiber 160. Fiber 160 can be used to pass light beams $B_1$, $B_2$ through a slit formed by a gate of fiber 160 to form lines $L_1$, $L_2$ (FIG. 2) on the desired target T.

System 100 may include a processor 302 that is operatively coupled to a display 306. In some examples, processor 302 and display 306 may be disposed within a single handheld unit, such as, e.g., a tablet computer with a user interface having a capacitive input. In other examples, processor 302 and display 306 may be modular and may connect to one another by any suitable mechanism. Display 306 may be any graphical user interface, such as a touch-screen input device that allows a user to send commands to processor 302. In other examples, a mouse and/or keyboard (not shown) may be operatively coupled to processor 302. Multiple display devices (with or without input capability) may be deployed at alternate sites in or out of the operating suite. This may include video output streams for broadcast to alternate pre-exiting/third party displays/locations.

Information related to status and components of system 100 may be stored in computer-readable memory that is accessible by processor 302 or a remote computing system using conventional data communication protocols. The memory may be local memory or the memory in which the information is stored may be remote from system 100. Processor 302 can access the remote memory using conventional data communication techniques, such as over network 340.

Processor 302 may be coupled to electronics 308, an endoscopic device, a fluoroscope 312, a patient monitoring device 320, as well as any other component or instrument to analyze target T. Processor 302 may be generally configured to accept information from the system and system components, and process the information according to various algorithms to produce control signals for analyzing images of the target T as well as control electronics 308, endoscopic device 310, fluoroscope 312, patient monitoring device 320, and the like. The processor 302 may accept information from the system 100 and system components, process the information according to various algorithms, and produce information signals that may be directed to target T, analyze one or more images from target T, modify the one or more images from target T, determine visual indicators, and communicate related information to one or more digital displays (e.g., a user interface) in order to inform a user of the system status, component status, procedure status or any other useful information (e.g., size of target T) that is being monitored by the system. The processor 302 may be a digital IC processor, analog processor or any other suitable logic or control system capable of performing image processing algorithms, target analysis algorithms, and/or control algorithms, during operation of system 100.

Electronics 308 may include an optical energy source, such as a holmium (Ho) laser source, a holmium:YAG (Ho:YAG) laser source, a neodymium-doped:YAG (Nd:YAG) laser source, a semiconductor laser diode, a potassium-titanyl phosphate crystal (KTP) laser source, a carbon dioxide ($CO_2$) laser source, an Argon laser source, an Excimer laser source, a diode laser source, or another suitable laser source. In some examples, the laser source may be a laser diode. The laser diode may illuminate a target area with a beam of light that can pass through a slit formed by gates 163 (e.g., a vertical line), and may be mounted at the distal end of a catheter, a probe, or other suitable elongate member, such as, e.g., an endoscopic member. In some examples, a high-power LED module (e.g., super-luminescent) may be used in place of a laser source. In some examples, an intense, pulsed light source may be used in place of a laser source. Electronics 308 may also include an imaging processing unit (IPU) (e.g., unit 316) as well as amplifier 314.

Figure 5A:
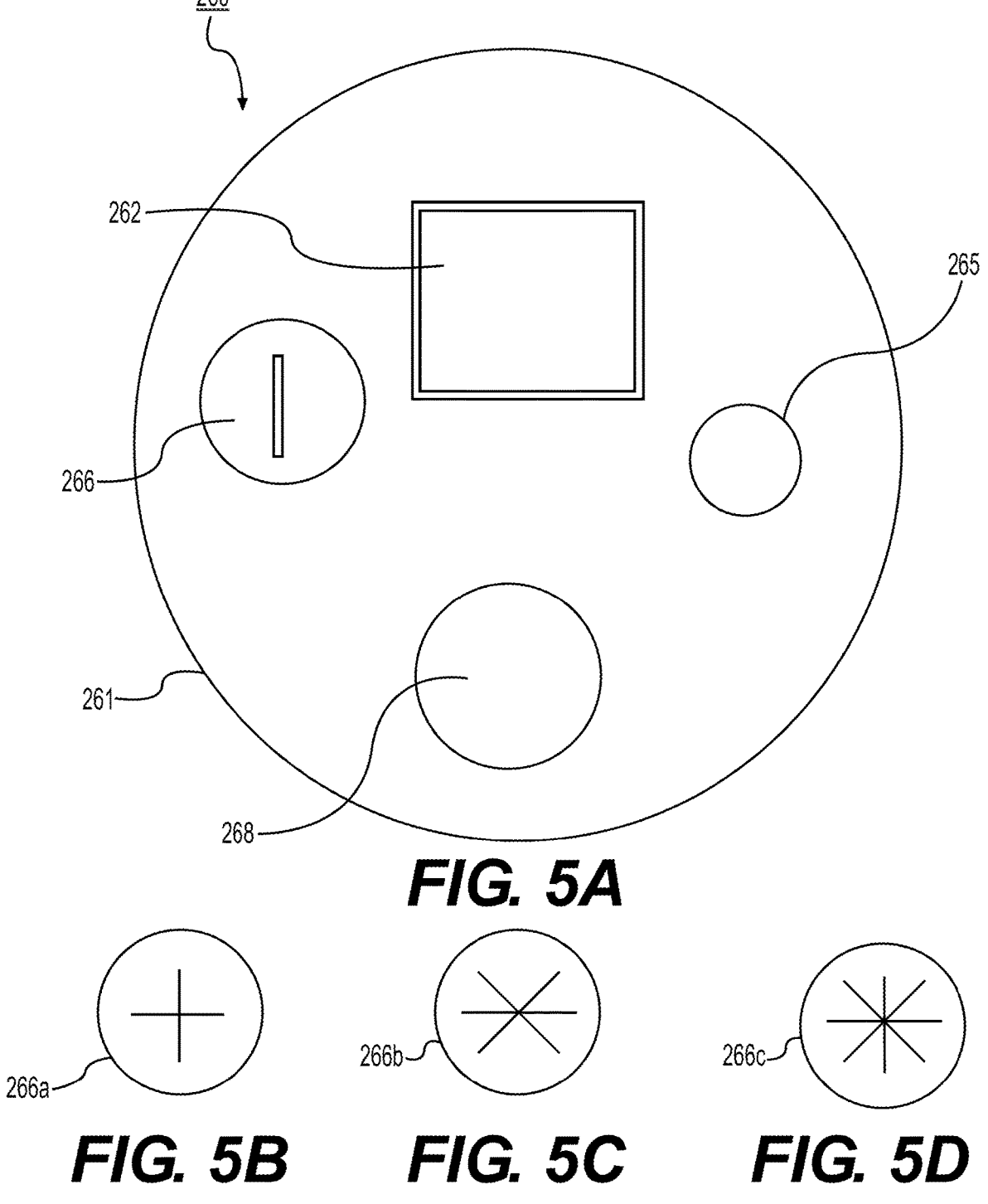
FIG. 5A illustrates a front plan cross-sectional view of another exemplary distal tip of the system shown in FIG. 1 in a first configuration.

In an example, electronics 308 may include a pneumatic control device for performing lithotripsy procedures by direct contact of a probe with a target T (e.g., through use of module 266 of FIG. 5A). In this example, processor 302 may control air pressure and frequency as well as irrigation activation and flowrate. The processor 302 may also be able to connect via the network 340 (and to server 342) and obtain patient related data from the HIS, PACS and EMR. This data can then be processed and displayed on display 306. The system may also allow the processor 302 to send updated data based on the procedure statistics and information back to the HIS, PACS and EMR.

In this respect, processor 302 may be coupled to one or more servers 342 via a network 340, such as, the Internet. One or more servers 342 can provide information to processor 302 such as, e.g., electronic medical records of the patient. The records may include standard medical and clinical data gathered by one or more health care providers for the patient, and may constitute a comprehensive medical history for the patient. The electronic medical records may include patient information pertinent to the physician performing a lithotripsy procedure, such as, previous history of stones, allergies to anesthesia, whether the patient is on blood thinners, among other information.

Endoscopic device 310 may be any suitable endoscopic member, such as, e.g., an endoscope, a ureteroscope, a nephroscope, a colonoscope, a hysteroscope, a uteroscope, a bronchoscope, a cystoscope, a sheath, or a catheter. Monitoring device 320 may include sensors configured to measure the blood pressure, pulse rate, temperature, and peripheral capillary oxygen saturation ($S_pO_2$), among other patient vitals. Portions of device 320 may be disposed on the skin of the patient, within the patient, or may be positioned off of the patient.

Figure 2:
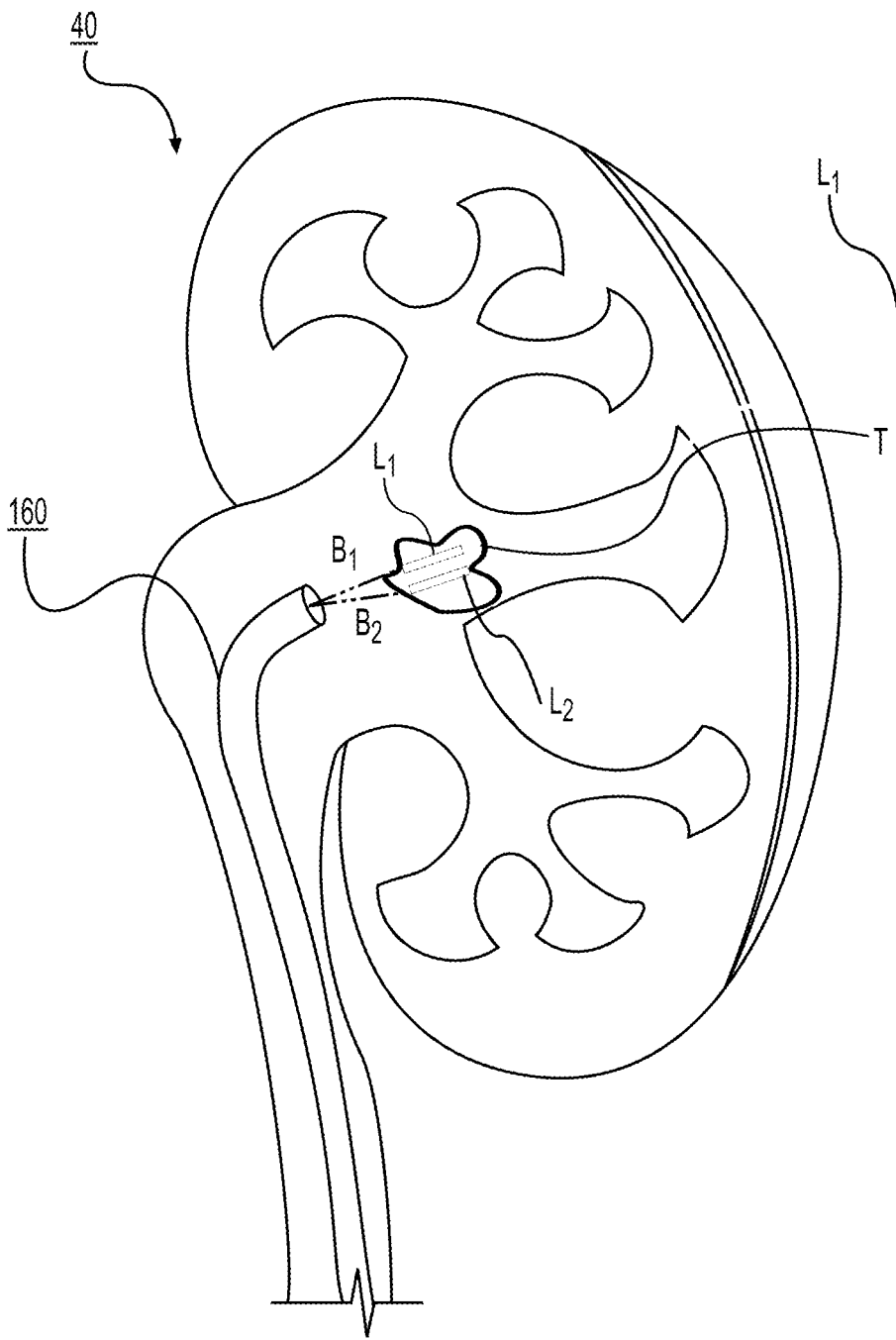
FIG. 2 illustrates a schematic view of an exemplary method of using the system of FIG. 1.

With reference to FIG. 2, fiber 160 is shown having been advanced within a urinary tract 40 to analyze target T. An operator may insert fiber 160 within the urinary tract 40 though a natural orifice or an incision. The operator may then maneuver fiber 160 within range of target T and emit beams $B_1$, $B_2$ through a slit to form a plurality of lines $L_1$, $L_2$ on target T.

Figure 3:
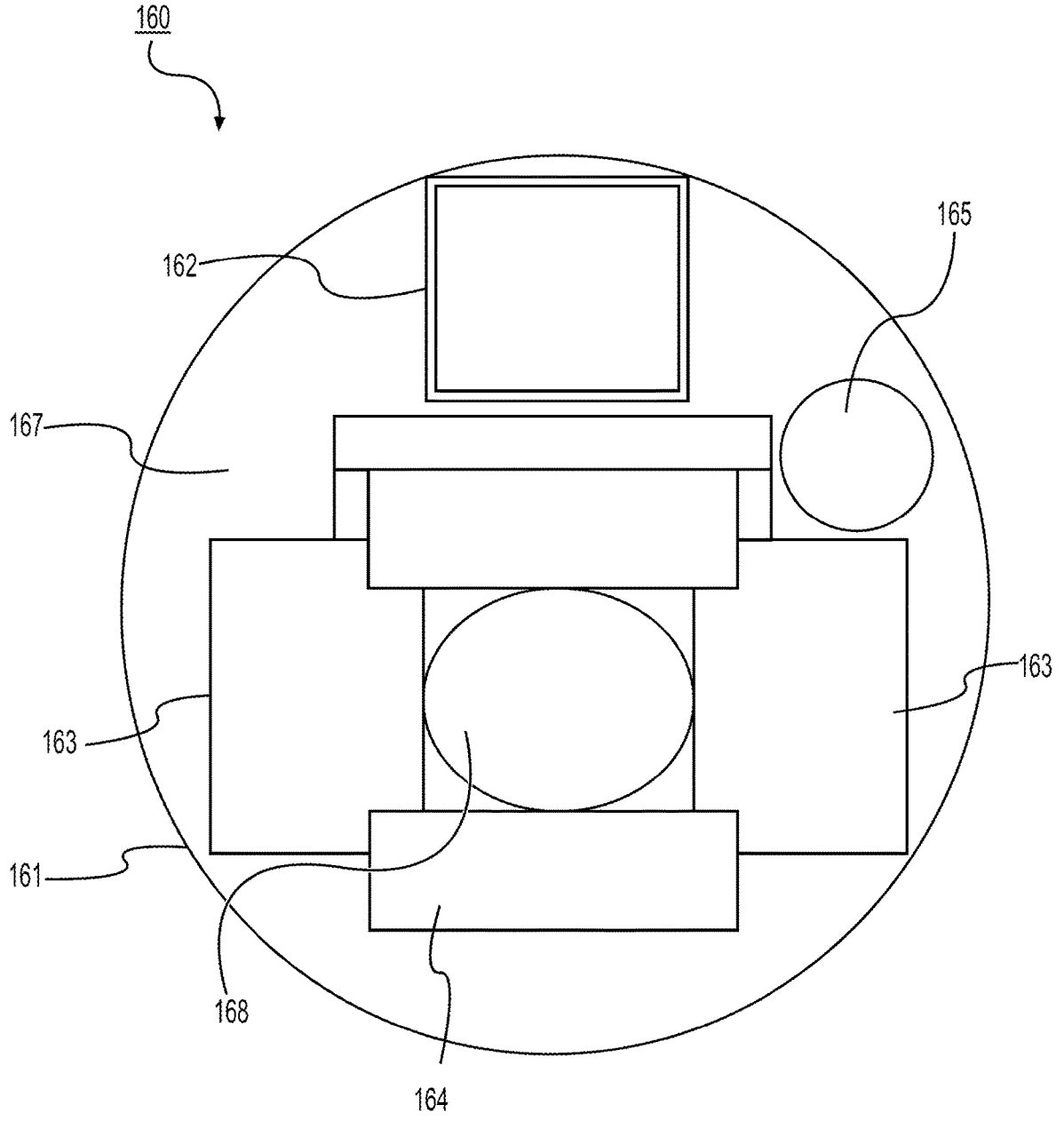
FIG. 3 illustrates a front plan cross-sectional view of a distal tip of the system shown in FIG. 1 in a first configuration.

With reference to FIG. 3, a close-up cross-sectional view is shown of a distal end at section 3-3 of fiber 160. Fiber 160 can be a multiple core fiber with an outer shell 161 with a lumen passing therethrough. Fiber 160 can be configured to deliver energy 127 at a distal end towards target T. Fiber 160 can include at least two fiber cores through which components, such as optical module 168, Power-Over-Fiber (POF) 165, and other components, can be run.

In certain aspects, fiber 160 can include at least one optical module 168 that extends axially within (e.g., a laser fiber and/or an LED fiber). Module 168 can include one or more lasers and/or LED modules positioned in a light source channel of fiber 160 configured to receive light or laser energy at a proximal end, and transmit light or laser energy to a distal end. In some aspects, module 168 can be configured to carry light from one or more proximally-located light sources, such as one or more laser light emitting diodes. Module 168 may receive energy transmitted from energy from electronics 308, and may deliver the received energy via energy 127 to target T.

An imaging device 162 (e.g., a camera) may also be included within shell 161 and may include any suitable device configured to provide images to processor 302 (e.g., a camera, a CMOS imaging sensor, other solid state device and one or more glass or polymeric lenses that produce electronic image signals representative of an image of the tissue or other objects in front of the device 162). Device 162 may be a low light sensitive, low noise video VGA, CMOS, color imager or higher resolution sensor such as SVGA, SXGA, or XGA. Video output of device 162 may be in any conventional format including PAL, NTSC or high definition video format, and may be transmitted to processor 302 by any wired or wireless mechanism.

A slit gate 163 can be included at the distal end of fiber 160 and be configured to open or close so as to expose module 168 to control energy delivery therefrom. Gate 163 can be distal of guide 164, which can be configured to allow gate 163 to slide inwards and away from module 168. In some aspects, gate 163 can be moved or otherwise actuated by guide 164 form a slit 169 (e.g., when both gates 163 move towards each other). Guide 164 can be a micro-electro mechanical system (MEMS) actuator, such as a micro gear-pinion or electrostatic or magnetic actuator. Gate 163 can include at least two portions oriented facing the other to create a slit through which energy 127 can pass to form beams $B_1$, $B_2$ to focus on target T. In some examples, gate 163 can include at least two rectangular portions that can actuate from an open state (FIG. 3) to advancing towards each other to form slit 169 in FIG. 4. It is understood that in the open state of gate 163, optical module 168 can be used to perform procedures separate from sizing or otherwise analyzing target T. For example, optical module 168 can be used to perform lithotripsy (e.g., to blast target T with laser energy) by move gates 163 fully open to expose module 168.

Figure 4:
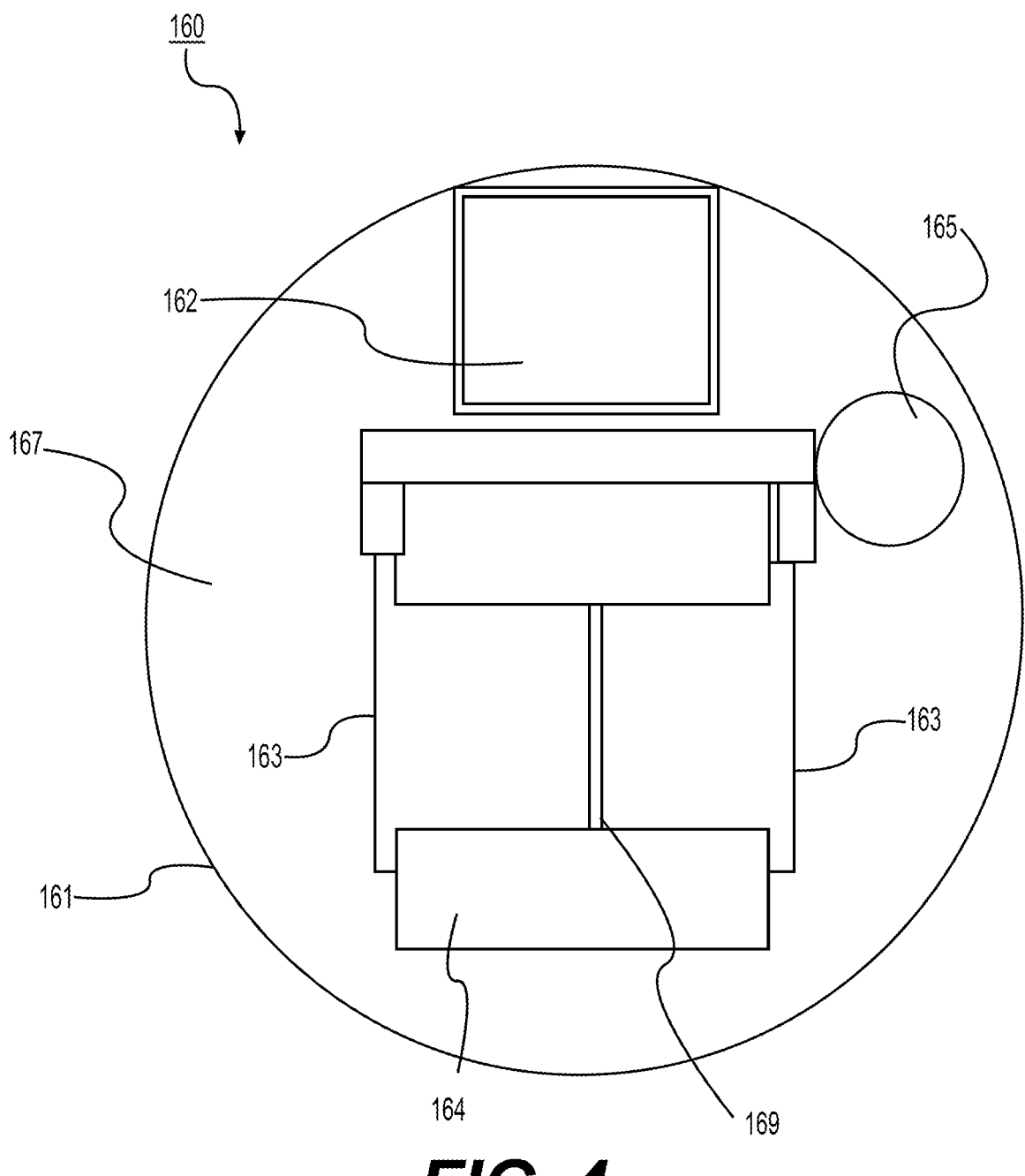
FIG. 4 illustrates a front plan cross-sectional view of a distal tip of the system shown in FIG. 1 in a second configuration.

While gate 163 is depicted in FIGS. 3-4 with at least two rectangular members to form slit 169, gate 163 is not so limited and other shapes are contemplated to form slit 169, including but not limited to rounded members, crescent shaped members, hemispherical shaped members, or any other shape capable of opening and closing to form a slit to focus beams $B_1$, $B_2$ on target T to form lines $L_1$, $L_2$ facing each other so as to modify energy 127 into beams.

In FIG. 4 with slit 169 formed and since module 168 can be a multi-core fiber, module 168 can deliver energy 127 to corresponding target T with beams $B_1$, $B_2$ being formed as they pass from respective fibers module 168. Slit 169 can modify the shape of beams $B_1$, $B_2$ from a relatively dot-like shape to form the lines dual $L_1$, $L_2$ on target T, as explained and depicted more clearly in FIGS. 7A-8E. These lines $L_1$, $L_2$ can be wrapped around target T to provide visual topography and by, e.g., calibrating device 162 with respect to lines $L_1$, $L_2$, the distance from target T to the distal tip of fiber 160 can be determined from the spacing between lines $L_1$, $L_2$. As explained below, with this information the size of target T can be determined.

In some aspects, processor 302 can be used by an operator to manage system 100 and perform other functions, such as opening or closing gate 163, as illustrated between FIGS. 3-4, as well as actuating energy delivery directed from module 168 towards target T. It is understood that components of the herein disclosed system, including those of fiber 160 such as module 168, can be packaged within a handle of a ureteroscope. Processor 302 can be configured to execute program instructions stored in memory of system 100, or another location, to perform various functions in accordance with embodiments described herein. Further, it is understood that processor 302 can be located remotely from system 100 and may also be used to perform various functions described herein.

With reference to FIG. 5A, another cross-section view plan view of a fiber 260 is shown having shell 261 that can contain elements of fiber 260 and extend along its entire length. It is contemplated that fiber 260 of FIG. 5A could be used in place of or in addition to fiber 160 of system 100 so that an operator can use the illustrated system to analyze target T while also performing lithotripsy procedures. Module 268 can be included and can extend axially within fiber 260. Module 268 can be configured for use in measuring a size of target T, similar to module 168, and include one or more lasers or LED modules. Fiber 260 can also include a second optical module 266, which can be used for lithotripsy. Having multiple modules 266, 268 in fiber 260 is particularly advantageous as the operator can check the size of target T at the same time during lithotripsy procedure(s). Like fiber 160, fiber 260 can also include imaging device 262 and one or more PoF fibers 265.

FIG. 5B shows an optional slit pattern of module 266a with a crisscross (e.g., two lines that form a T or plus sign) or t-shaped slit formed by gates 263a. FIG. 5C shows an optional slit pattern of module 266b with at least three intersecting lines having a common intersection similarly formed by corresponding moving and/or fixed gates 263b. Preferably, all slit patterns of this disclosure can have at least dual lines formed from one slit that can be used to determine the distance and other lines of the slit pattern can be single lines from other slits. The intersection can be a center of each of the lines. FIG. 5D shows an optional slit pattern of module 266c with more than two intersecting lines, including at least three intersecting lines, at least four intersecting lines, and so forth, in each aspect having a common central intersection similarly formed by moving and/or fixed gates 263c.

Figure 6A:
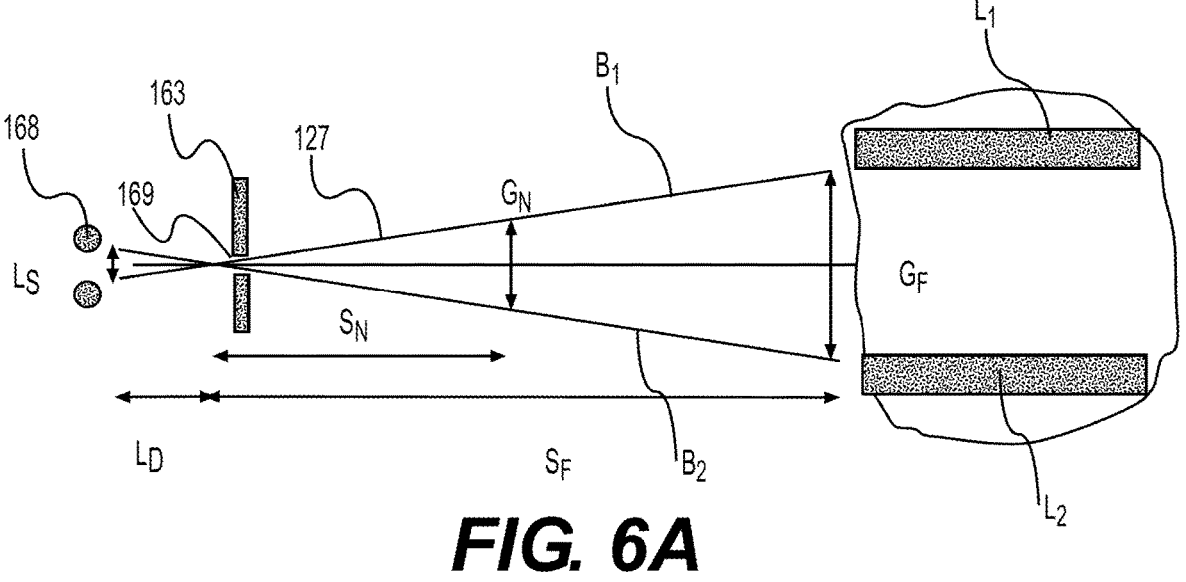
FIG. 6A is a diagram explaining a distance measuring operation of the system of FIG. 1.

FIG. 6A shows a schematic overview of a measuring operation to analyze a size of target T using lines $L_1$, $L_2$ formed by passing beams $B_1$, $B_2$ through gate 163. Here, module 168 operates according to the algorithm of measuring the distance between module 168, gates 163, and lines $L_1$, $L_2$ directed on target T by module 168. Light can be reflected and detected in one or more target images by device 162. Such operations and related algorithm(s) can be performed by or in connection with processor 302. For example, processor 302 can cause module 168 to deliver energy 127 and employ distance measuring algorithms related to light passing through slit 169 formed by gates 163 that utilize laser model triangle similarities, according to the following:

$$F = P \times \frac{D_W}{w}$$

where F is focal length of imaging device 162, P is pixel of imaging device 162, $D_w$ is the distance from target T, and w is width of the target T. It is understood that lines $L_1$, $L_2$ can be initially detected in a target image taken and/or received by module 168 (e.g., via device 162), as in the operations of FIGS. 7A-8E.

Figure 6B:
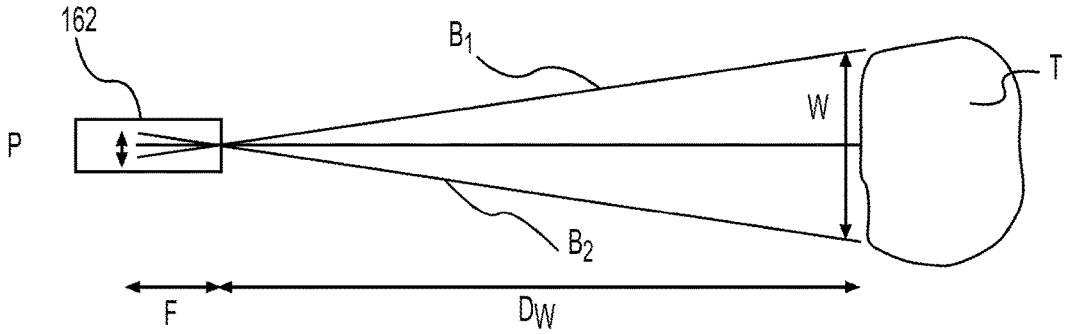
FIG. 6B is a diagram explaining a distance measuring operation of the system of FIG. 1.

FIG. 6B shows a schematic of the operation premised on the function of focal length F. Turning back to FIG. 6A, since the focal length F of imaging device 162 in this example is known, as well as laser spacing $L_s$ and laser distance $L_D$, the remaining elements of FIG. 6A can be determined by processor 302, according to the following:

$$F = \frac{S_N}{G_N} = \frac{S_F}{G_F} = \frac{L_D}{L_S}$$

where $S_N$ is the object near distance, $G_N$ is the near laser gap, $S_F$ is the object far distance, and $G_F$ is the far laser gap. In some aspects, laser distance $L_D$ in the algorithm of FIG. 6A can be replaced by an optics for consistent spacing from the slit formed by gate 163. Based on the measuring operation(s), a size of target T can be determined and communicated to an operator in order to, among other things, promptly and safely inform treatment received by patient premised on target sizing accuracy. That is, the foregoing operations can accurately measure the distance between module 168 and target T and therefore size of target T in a short time at relatively high precision.

In another example, a correlation between the line gap and the depth can be performed by processor 302 by using a reference table or database. For example, g(ø)=f(Z), where f(Z) function is a complex formula with no numerical solution. Processor 302 can perform a calibration step (e.g., calibrating of device 162) to determine a relationship between g(ø) and Z. For example, when g(ø)=5 pixels, the system 100 can measure Z=5 mm, when g(ø)=10 pixel, thereby measuring Z=8 mm, etc. The reference table or database can serve as reference during the lithotripsy procedure(s).

Figures 7A, 7B, 7C, 7D, 7E, 7F:
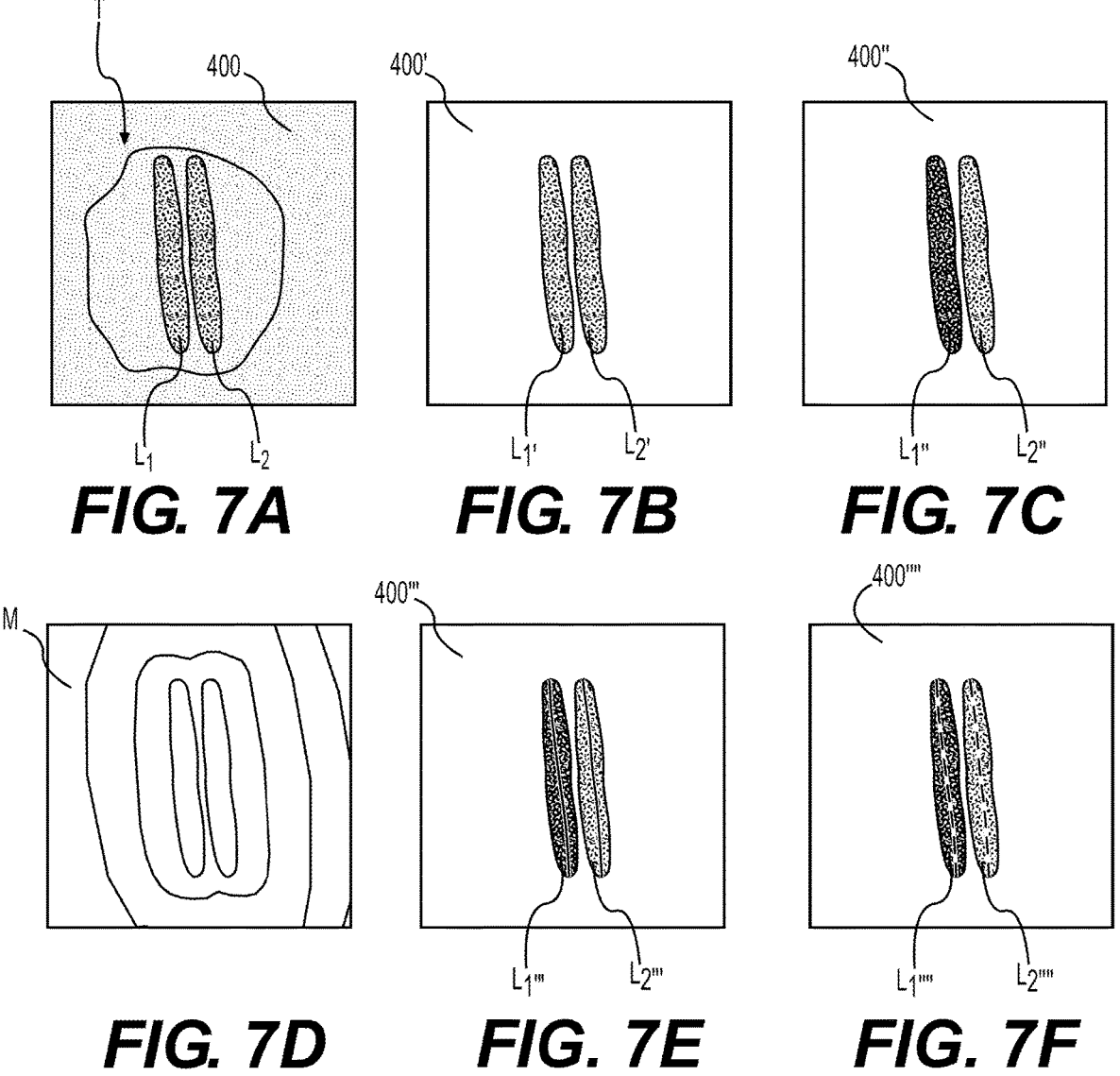
FIG. 7A illustrates an example target image of a kidney stone taken by the optical fiber.
FIG. 7B illustrates the example target image of FIG. 7A in a second state.
FIG. 7C illustrates the example target image of FIG. 7A in a third state.
FIG. 7D illustrates the example target image of FIG. 7A presented in a distance map.
FIG. 7E illustrates the example target image of FIG. 7A in a fourth state.
FIG. 7F illustrates the example target image of FIG. 7A in a fifth state.
Figures 8A, 8B, 8C, 8D, 8E:
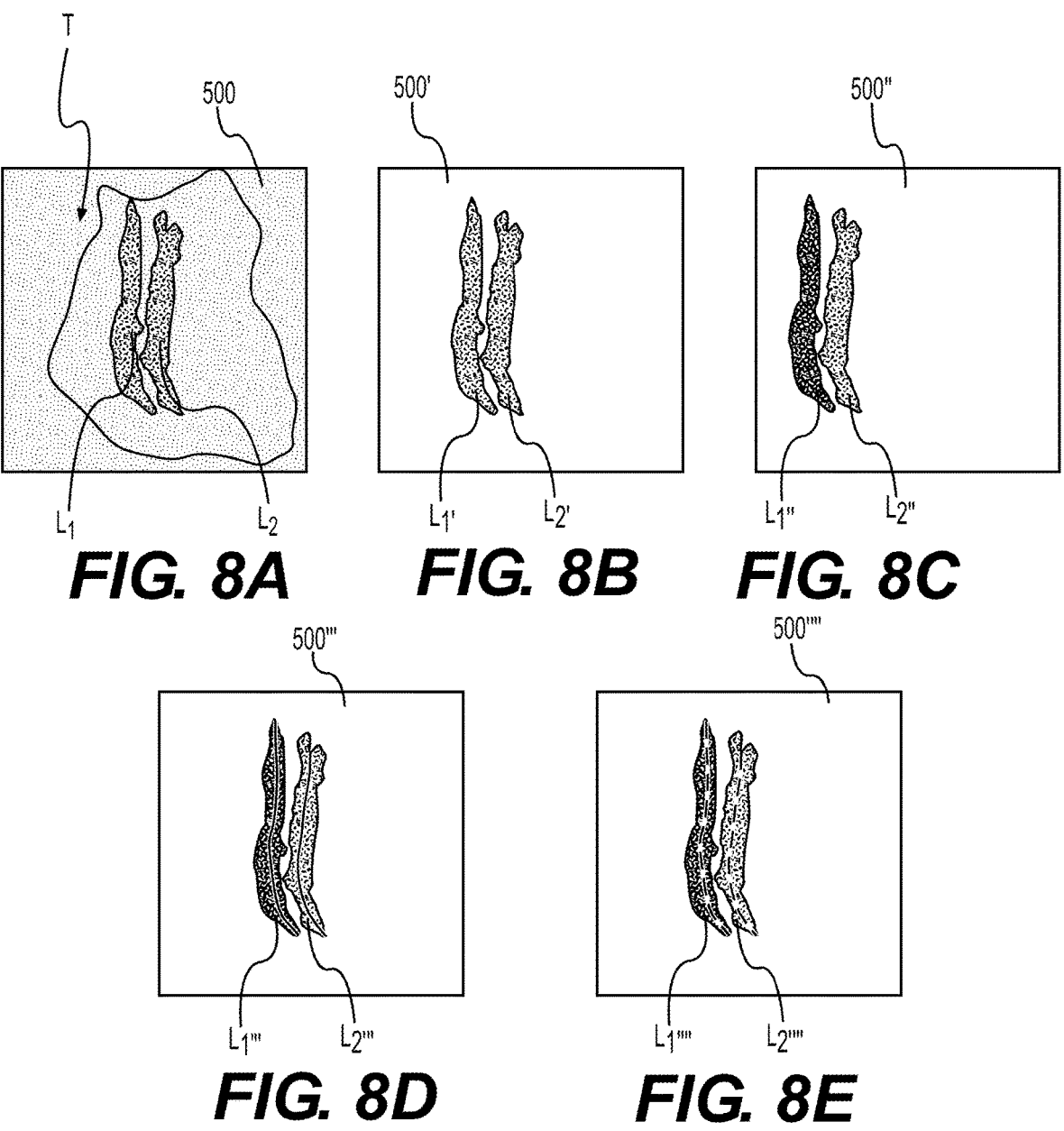
FIG. 8A illustrates an example target image of a kidney stone taken by the optical fiber.
FIG. 8B illustrates the example target image of FIG. 8A in a second state.
FIG. 8C illustrates the example target image of FIG. 8A in a third state.
FIG. 8D illustrates the example target image of FIG. 8A in a fourth state.
FIG. 8E illustrates the example target image of FIG. 8A in a fifth state.

FIGS. 7A to 7F illustrate examples of one sequence of measuring target T. In particular, FIG. 7A illustrates an example target image 400 of target T (e.g., a kidney stone) taken by device 162 of fiber 160 in an initial state after fiber 160 has been advanced within patient to the treatment site. Image 400 shows a coarse outline of target T as it exists in vivo within the patient with lines $L_1$, $L_2$ having been focused onto target T. Lines $L_1$, $L_2$ as shown are relatively straight. As can also be seen, a gap or spacing is formed between lines $L_1$, $L_2$. As the lines are much brighter than the surroundings, a simple threshold algorithm (FIG. 7B) figure) can segment the lines from the frame. In FIG. 7B specifically, image 400 has been modified to image 400' by one or more image processing algorithms performed by processor 302. In particular, a threshold algorithm can take lines $L_1$, $L_2$, which are brighter than the surroundings of image 400, and modify image 400 to form image 400' so as to segment the lines from the frame of target T thereby forming a segmented pair of lines $L_1'$, $L_2'$.

While not shown, the background in FIGS. 7B through 7F can be dark or otherwise opaque to facilitate viewing the profile of target T, but not too bright that it washes out lines $L_1'$, $L_2'$. A connected component analysis can be performed on image 400', as in FIG. 7C, to separate the two lines $L_1'$, $L_2'$ and form lines $L_1''$, $L_2''$. In some aspects, lines $L_1''$, $L_2''$ can be extracted from segmented lines $L_1'$, $L_2'$ (FIG. 7E and FIG. 7F). To extract lines $L_1''$, $L_2''$, a distance map M of FIG. 7D can be calculated first. The distance map M shown in FIG. 7D can give the distance for each pixel in the segmented lines $L_1'$, $L_2'$ to its boundaries in a way similar to a contour map.

In FIG. 7E, center lines are now extracted modifying lines $L_1''$, $L_2''$ to form segmented lines $L_1'''$, $L_2'''$. Lines $L_1'''$, $L_2'''$ of FIG. 7E can be along the ridges of the distance map of FIG. 7D. In certain aspects, the further the pixel is away from the boundary, the larger its distance value will be. Afterwards, In FIG. 7F, points with certain intervals are taken along $L_1'''$, $L_2'''$ to form lines $L_1''''$, $L_2''''$. In particular, intervals are taken from the center lines and the shortest distances from each point of $L_1''''$ to the points of the other center line $L_2''''$ are calculated. The distances can then be averaged to precisely calculate the gap between the two lines.

While the operation of FIGS. 7A to 7E is shown where lines $L_1$, $L_2$ are depicted relatively straight, planar, and/or otherwise non-curved, it is also contemplated that similar operations can be performed to determine a size of target T where the surface of the target T is relatively uneven or otherwise asymmetrically shaped, as shown in FIGS. 8A to FIG. 8E, which shows target image 500 taken of an uneven target T and modified through a similar operation of FIGS. 7A-7E, in order to determine target T size and other related information. While not shown in FIGS. 8A to 8E, it is contemplated that a distance map M can also be used to extract center lines to provide the distance for each pixel in segment lines to respective boundaries, just as in FIG. 7D.

In some examples, the spacing between lines $L_1$, $L_2$ as shone on target T can vary with respect to the distance of device 162 and/or module 168 from target T. For example, the nearer the device 162 and/or module 168 to target T, the smaller the gap or spacing can be between lines $L_1$, $L_2$. On the other hand, the further the device 162 and/or module 168 from target T, the larger the gap or spacing can be between lines $L_1$, $L_2$. This determined gap or spacing between lines $L_1$, $L_2$ can determine how far device 162 and/or module 168 is away from target T. Further, this determined gap or spacing between lines $L_1$, $L_2$, as well as spacing between fibers of fiber 160, slit 169 thickness, and the length of lines $L_1$, $L_2$ as shown above in FIGS. 6A-6B, can facilitate precise size determination of target T.

Figure 9:
FIG. 9 depicts a flow diagram of a method of using a system to analyze a target according to certain aspects of this disclosure.
Figure 9:
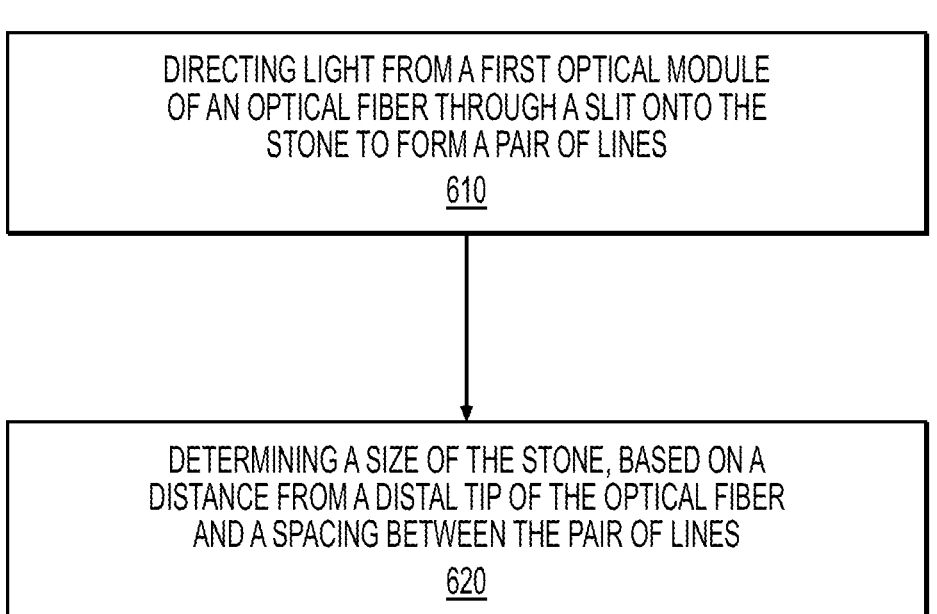

FIG. 9 depicts a method or use 600 of any of the herein disclosed systems. Step 610 of method 600 can include directing light from a first optical module of an optical fiber through a slit onto the stone to form a pair of lines. Step 620 of method 600 can include determining a size of the stone, based on a distance from a distal tip of the optical fiber and a spacing between the pair of lines. Method 600 can end after step 620. In other embodiments, additional steps according to the examples described above can be performed.

FIG. 10 depicts a method or use 700 of any of the herein disclosed systems. Step 710 of method 700 can include using a threshold algorithm to segment the pair of lines from the one or more frames. Step 720 of method 700 can include using connected component analysis to separate the segmented pair of lines. Step 730 of method 700 can include extracting a center line from each of the segmented pair of lines. Step 740 of method 700 can include extracting a plurality of points with certain interval from each of the center lines. Step 750 of method 700 can include calculating a shortest distance from each point of one of the center lines to the plurality of points of the other center line. Step 760 of method 700 can include averaging the shortest distance to calculate the spacing between the pair of lines. Method 700 can end after step 760. In other embodiments, additional steps according to the examples described above can be performed.

The systems, methods, and operations disclosed herein may enable operators to make faster and smarter decisions to enhance clinical outcomes, reduce procedure time, reduce cognitive loads required during procedures, and reduce overall procedure costs. Other aspects and embodiments of the present disclosure will be apparent to those skilled in the art from consideration of the specification and practice of the embodiments disclosed herein. While certain features of the present disclosure are discussed within the context of exemplary procedures, the compositions, systems, and methods may be used for other medical procedures according to the general principles disclosed. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein. It is intended that the specification and examples be considered as exemplary only, with a true scope and spirit of the present disclosure being indicated by the following claims.

What is claimed is:

1. A system for analyzing in vivo a kidney stone, the system comprising:
an optical fiber comprising a first optical module, a camera, and a slit gate, the slit gate having a first gate member and a second gate member capable of moving relative to one another to transition the slit gate between an open state and a closed state to form a slit in the closed state;
at least one processor; and
at least one storage medium having encoded thereon executable instructions that, when executed by the at least one processor, cause the at least one processor to carry out a method comprising:
directing light from the first optical module through the slit onto the stone to form a pair of lines with a spacing formed between the pair of lines;
receiving an image of the stone captured by the camera, the image including the pair of lines formed on the stone;
extracting, from the image, a first center line from a first line of the pair of lines and a second center line from a second line of the pair of lines;
extracting a first plurality of points with particular intervals from the first center line and a second plurality of points with the particular intervals from the second center line;
determining a plurality of shortest distances, wherein the plurality of shortest distances include a shortest distance from each point of the first plurality of points to the second plurality of points;
determining a distance of the spacing between the pair of lines based on an average of the plurality of shortest distances; and
determining a size of the stone, based on a distance from a distal tip of the optical fiber to the stone and the distance of the spacing between the pair of lines.

2. The system of claim 1, wherein the slit is a vertical line or crossed lines.

3. The system of claim 1, wherein the slit comprises at least three lines with a common intersection.

4. The system of claim 1, wherein the optical fiber comprises a second optical module configured to be used for lithotripsy.

5. The system of claim 4, wherein the slit gate is configured to be in the open state when the second optical module of the optical fiber is actuated for lithotripsy use.

6. The system of claim 1, wherein the optical fiber is a multiple core fiber comprising at least two fiber cores lit by a light-emitting diode (LED) module inside a handle of a ureteroscope.

7. The system of claim 1, wherein extracting, from the image, the first center line and the second center line comprises:
using a threshold algorithm to segment the pair of lines from the image; and
using connected component analysis to separate the segmented pair of lines into the first line and the second line from which the first center line and the second center line are respectively extracted.

8. The system of claim 1, wherein the first gate member and the second gate member of the slit gate are configured to be moved toward each other to transition the slit gate from the open state to the closed state to cause the slit to be formed between the first gate member and the second gate member.

9. The system of claim 1, wherein the optical fiber further comprises a guide configured to actuate movement of the first gate member and the second gate member relative to one another.

10. The system of claim 9, wherein the method carried out by the at least one processor further comprises:
causing the guide to actuate the movement.

11. The system of claim 1, wherein directing the light further comprises:
directing two light beams from the first optical module through the slit onto the stone and modifying, by the slit, a shape of the two light beams to form the pair of lines with the spacing between the pair of lines on the stone.

12. The system of claim 11, wherein the optical fiber is a multiple core fiber with at least two fiber cores.

13. The system of claim 11, wherein the shape of each of the two light beams prior to the modifying by the slit is a dot.

14. The system of claim 1, wherein determining the size of the stone comprises:
determining the distance from the stone to the distal tip of the optical fiber based on the distance of the spacing between the pair of lines.

15. A system for analyzing in vivo a kidney stone, the system comprising:
an optical fiber comprising a first optical module, a camera, and a slit gate, the slit gate being capable of moving between an open state and a closed state to form a slit in the closed state;
at least one processor; and
at least one storage medium having encoded thereon executable instructions that, when executed by the at least one processor, cause the at least one processor to carry out a method comprising:
causing the first optical module to direct light through the slit and onto the stone to form a pair of lines on the stone with a spacing formed between the pair of lines;
receiving an image of the stone captured by the camera, the image including the pair of lines formed on the stone;
processing the image to extract a first center line from a first line of the pair of lines and a second center line from a second line of the pair of lines;
determining, as a distance of the spacing between the pair of lines, a distance from the first center line to the second center line by:
extracting a first plurality of points with particular intervals from the first center line;
extracting a second plurality of points with the particular intervals from the second center line;
calculating a plurality of shortest distances, the plurality of shortest distances including a shortest distance from each point of the first plurality of points to the second plurality of points; and
averaging the plurality of shortest distances; and
determining a size of the stone, based on a distance from the stone to a distal tip of the optical fiber and the distance of the spacing between the pair of lines.

16. The system of claim 15, wherein processing the image to extract the first center line and the second center line comprises:
using a threshold algorithm to segment the pair of lines from the image;

using connected component analysis to separate the seg-
mented pair of lines into the first line and the second
line; and extracting the first center line and the second center line
from each of the first line and the second line, respec-
tively.

17. A system for analyzing in vivo a kidney stone, the
system comprising:

an optical fiber comprising a first optical module, a
camera, and a slit gate, the slit gate capable of moving
between closed and opened states to form a slit;

at least one processor; and at least one storage medium having encoded thereon
executable instructions that, when executed by the at
least one processor, cause the at least one processor to
carry out a method comprising:

directing light from the first optical module through the
slit onto the stone to form a pair of lines with a
spacing formed between the pair of lines;

receiving, from the camera, one or more images of the
stone;

calculating the spacing between the pair of lines by
applying one or more image processing algorithms to
extract information from one or more frames of the one or more images, wherein applying the one or
more image processing algorithms includes:

using a threshold algorithm to segment the pair of
lines from the one or more frames;

using connected component analysis to separate the
segmented pair of lines;

extracting a center line from each of the segmented
pair of lines;

extracting a plurality of points with certain intervals
from each of the center lines;

calculating a shortest distance from each point of one
of the center lines to the plurality of points of the
other center line; and averaging the shortest distances to calculate the
spacing between the pair of lines; and determining a size of the stone, based on a distance
from a distal tip of the optical fiber to the stone and
the spacing between the pair of lines.

18. The system of claim 17, wherein determining the size
of the stone comprises:

determining the distance from the distal tip of the optical
fiber to the stone based on the averaged shortest dis-
tances calculated for the spacing between the pair of
lines.

*    *    *    *    *